(12) United States Patent
Johnson et al.

(10) Patent No.: US 10,188,446 B2
(45) Date of Patent: Jan. 29, 2019

(54) RESONANT INVERTER

(71) Applicant: COVIDIEN LP, Mansfield, MA (US)

(72) Inventors: Joshua H. Johnson, Arvada, CO (US); James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 574 days.

(21) Appl. No.: 14/446,914

(22) Filed: Jul. 30, 2014

(65) Prior Publication Data
US 2015/0105767 A1    Apr. 16, 2015

Related U.S. Application Data

(60) Provisional application No. 61/891,811, filed on Oct. 16, 2013.

(51) Int. Cl.
| | |
|---|---|
| *A61B 18/12* | (2006.01) |
| *H01F 27/00* | (2006.01) |
| *H02M 7/48* | (2007.01) |
| *H02M 7/5387* | (2007.01) |

(52) U.S. Cl.
CPC ....... *A61B 18/1206* (2013.01); *H01F 27/006* (2013.01); *H02M 7/48* (2013.01); *H02M 7/53871* (2013.01); *A61B 2018/1286* (2013.01); *H02M 2007/4815* (2013.01); *Y02B 70/1441* (2013.01)

(58) Field of Classification Search
CPC ........ H01F 27/006; H02M 2007/4815; H02M 7/48; H02M 7/53871; Y02B 70/1441; A61B 18/1206; A61B 2018/1286
See application file for complete search history.

(56) References Cited

U.S. PATENT DOCUMENTS

| | | | | |
|---|---|---|---|---|
| 3,824,432 A | * | 7/1974 | Gersing | F23Q 3/004 315/183 |
| 5,073,849 A | | 12/1991 | Morris | |
| 5,466,992 A | * | 11/1995 | Nemirow | H05B 41/2988 315/105 |
| 5,495,405 A | | 2/1996 | Fujimura et al. | |
| 5,841,239 A | | 11/1998 | Sullivan et al. | |
| 6,072,709 A | * | 6/2000 | Raets | H02M 3/28 307/28 |
| 6,320,490 B1 | * | 11/2001 | Clayton | H01F 30/10 336/170 |

(Continued)

FOREIGN PATENT DOCUMENTS

| | | |
|---|---|---|
| CN | 103259347 A | 8/2013 |
| CN | 103329398 A | 9/2013 |

(Continued)

OTHER PUBLICATIONS

European Search Report No. 14159839.1 dated Jul. 8, 2014.

(Continued)

*Primary Examiner* — Daniel W Fowler

(57) ABSTRACT

The present disclosure is directed to an electrosurgical generator including a resonant inverter having an H-bridge and a tank. The tank includes a transformer including a first core half, a second core half, a primary winding, and a secondary winding having a number of turns, wherein each turn is separated by a gap. The transformer is configured to provide a parallel capacitance based on the gap.

7 Claims, 5 Drawing Sheets

(56) References Cited

U.S. PATENT DOCUMENTS

| | | | |
|---|---|---|---|
| 6,344,979 B1* | 2/2002 | Huang | H02M 3/337 363/131 |
| 6,939,347 B2 | 9/2005 | Thompson | |
| D574,323 S | 8/2008 | Waaler | |
| 8,685,015 B2 | 4/2014 | Gilbert | |
| 2002/0183804 A1 | 12/2002 | Malaney et al. | |
| 2005/0286270 A1 | 12/2005 | Petkov et al. | |
| 2006/0043792 A1 | 3/2006 | Hjort et al. | |
| 2007/0129716 A1 | 6/2007 | Daw et al. | |
| 2007/0173808 A1 | 7/2007 | Goble | |
| 2008/0129222 A1* | 6/2008 | Chen | H05B 41/282 315/294 |
| 2008/0224809 A1* | 9/2008 | Zhang | H01F 3/12 336/170 |
| 2009/0036884 A1 | 2/2009 | Gregg et al. | |
| 2010/0114090 A1 | 5/2010 | Hosier | |
| 2010/0124035 A1 | 5/2010 | Bandholz et al. | |
| 2011/0063065 A1* | 3/2011 | Hugues Douglas | H01F 3/10 336/170 |
| 2011/0170321 A1 | 7/2011 | Schall et al. | |
| 2012/0095461 A1 | 4/2012 | Herscher et al. | |
| 2012/0098351 A1 | 4/2012 | Ross | |
| 2013/0023871 A1 | 1/2013 | Collins | |
| 2013/0267945 A1 | 10/2013 | Behnke, II et al. | |
| 2014/0104028 A1 | 4/2014 | Johnston | |
| 2015/0034406 A1 | 2/2015 | Hirose | |

FOREIGN PATENT DOCUMENTS

| | | |
|---|---|---|
| CN | 103329420 A | 9/2013 |
| DE | 179607 C | 3/1905 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1064047 A1 | 1/2001 |
| EP | 1366724 A1 | 12/2003 |
| EP | 1776929 A1 | 4/2007 |
| EP | 2469699 A2 | 6/2012 |
| EP | 2742888 A1 | 6/2014 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | S5928885 A | 2/1984 |
| JP | 60-064765 | 4/1985 |
| JP | 63 005876 A | 1/1988 |
| JP | H0767357 A | 3/1995 |
| JP | 2002-065690 A | 3/2002 |
| JP | 2005510050 A | 4/2005 |
| JP | 2005-185657 A | 7/2005 |
| JP | 2008218334 A | 9/2008 |
| JP | 2008227421 A | 9/2008 |
| JP | 2009-081183 A | 4/2009 |
| JP | 2011067590 A | 4/2011 |
| JP | 2012501696 A | 1/2012 |
| SU | 166452 | 11/1964 |
| SU | 727201 A2 | 4/1980 |
| WO | 96/39086 A1 | 12/1996 |
| WO | 9815317 A1 | 4/1998 |
| WO | 9947204 A1 | 9/1999 |
| WO | 02/11634 A1 | 2/2002 |
| WO | 02/45589 A2 | 6/2002 |
| WO | 03043034 A1 | 5/2003 |
| WO | 03/090635 A1 | 11/2003 |
| WO | 06/050888 A1 | 5/2006 |
| WO | 08/053532 A1 | 5/2008 |
| WO | 2012101906 A1 | 8/2012 |
| WO | 2013-125010 A1 | 8/2013 |
| WO | 2014-062357 A1 | 4/2014 |

OTHER PUBLICATIONS

European Search Report dated Jun. 29, 2015, issued in EP Application No. 14 18 5720.
Dalessandro L. et al., "Self-Capacitance of High-Voltage Transformers", IEEE Transactions on Power Electronics, Institute of Electrical and Electronics Engineers, USA, vol. 22, No. 5, (Sep. 1, 2007), pp. 2081-2092.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

(56) References Cited

OTHER PUBLICATIONS

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedance", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
European Examination Report in corresponding EP Application No. 14185720.1, dated Feb. 10, 2017, 6 pages.
Chinese Office Action dated Feb. 11, 2018 and issued in Chinese Patent Application No. 201410525872.X together with English translation.
Lixin, Tan, "Fundamental of Electric Circuit based on Project Orientation," Sep. 30, 2011, pp. 30-34 with brief English description.
Chinese Office Action dated Aug. 6, 2018 in corresponding Chinese Patent Application No. 201410525872.X, together with English translation.
Australian Examination Report dated Jun. 21, 2018 and issued in corresponding Australian Patent Application No. 2014218365.
Japanese Office Action dated Jun. 4, 2018 and issued in corresponding Japanese Patent Application No. 2014-189908 with English translation.
Third Office Action issued by the State Intellectual Property Office of the People's Republic of China dated Nov. 9, 2018 in corresponding Chinese Patent Application No. 201410525872.X with English translation.
Communication pursuant to Article 94(3) EPC and accompanying pages issued by the European Patent Office dated Nov. 9, 2018 in corresponding European Patent Application No. 14185720.1.

* cited by examiner

RESONANT INVERTER

CROSS REFERENCE TO RELATED APPLICATION

The present application claims the benefit of and priority to U.S. Provisional application Ser. No. 61/891,811, filed on Oct. 16, 2013, the entire contents of which are incorporated herein by reference.

BACKGROUND

1. Technical Field

The present disclosure relates to radiofrequency amplifiers that use phase-shifted full bridge resonant inverters. Particularly, the present disclosure is directed to reducing the cost and complexity of the resonant inverters.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. A source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated and the return electrode is placed remotely from the active electrode to carry the current back to the generator. In bipolar electrosurgery, one of the electrodes of the hand-held instrument functions as the active electrode and the other as the return electrode.

FIG. 1 is an example of a prior art electrosurgical generator that uses a phase-shifted full bridge resonant inverter to generate the electrosurgical energy needed to perform the electrosurgical procedure. The generator 100 includes a resonant inverter 102 and a pulse width modulation (PWM) controller 108. The resonant inverter 102 includes an H-bridge 104 an LCLC tank 106. The tank 106 includes a series inductor, a series capacitor, a parallel inductor, and a parallel capacitor. Because of the number of components in the tank 106, the cost and complexity of the resonant inverter is increased.

SUMMARY

This description may use the phrases "in an embodiment," "in embodiments," "in some embodiments," or "in other embodiments," which may each refer to one or more of the same or different embodiments in accordance with the present disclosure. As used herein, the term "generator" may refer to a device capable of providing energy. Such device may include a power source and an electrical circuit capable of modifying the energy outputted by the power source to output energy having a desired intensity, frequency, and/or waveform.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described data and/or algorithms may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In an aspect of the present disclosure, an electrosurgical generator includes a tank configured to output energy and an H-bridge configured to drive the tank. The generator also includes a transformer. The transformer has a first core half, a second core half, a primary winding, and a secondary winding having a number of turns, wherein each turn is separated by a gap. The transformer is configured to provide a parallel capacitance based on the gap.

In another aspect of the present disclosure, an electrosurgical generator includes a tank configured to output energy and an H-bridge configured to drive the tank. The generator also includes a transformer. The transformer includes a first core half, a second core half separated from the first core half by a first gap, a primary winding, and a secondary winding having a number of turns wherein each turn is separated by a second gap. The transformer is configured to provide a magnetizing inductance based on the first gap and a parallel capacitance based on the second gap.

In yet another aspect of the present disclosure, an electrosurgical generator includes a tank configured to output energy and an H-bridge configured to drive the tank. The generator also includes a transformer. The transformer includes a first core half, a second core half separated from the first core half by a first gap, a primary winding, and a secondary winding separated from the primary winding by a second gap. The secondary winding having a number of turns wherein each turn is separated by a third gap. The transformer is configured to provide a magnetizing inductance based on the first gap, a leakage inductance based on the second gap, and a parallel capacitance based on the third gap.

In the aspects described above, the electrosurgical generators include a bobbin coupled to the first core half and the second core half. Both the primary winding and the secondary winding are disposed on the bobbin.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
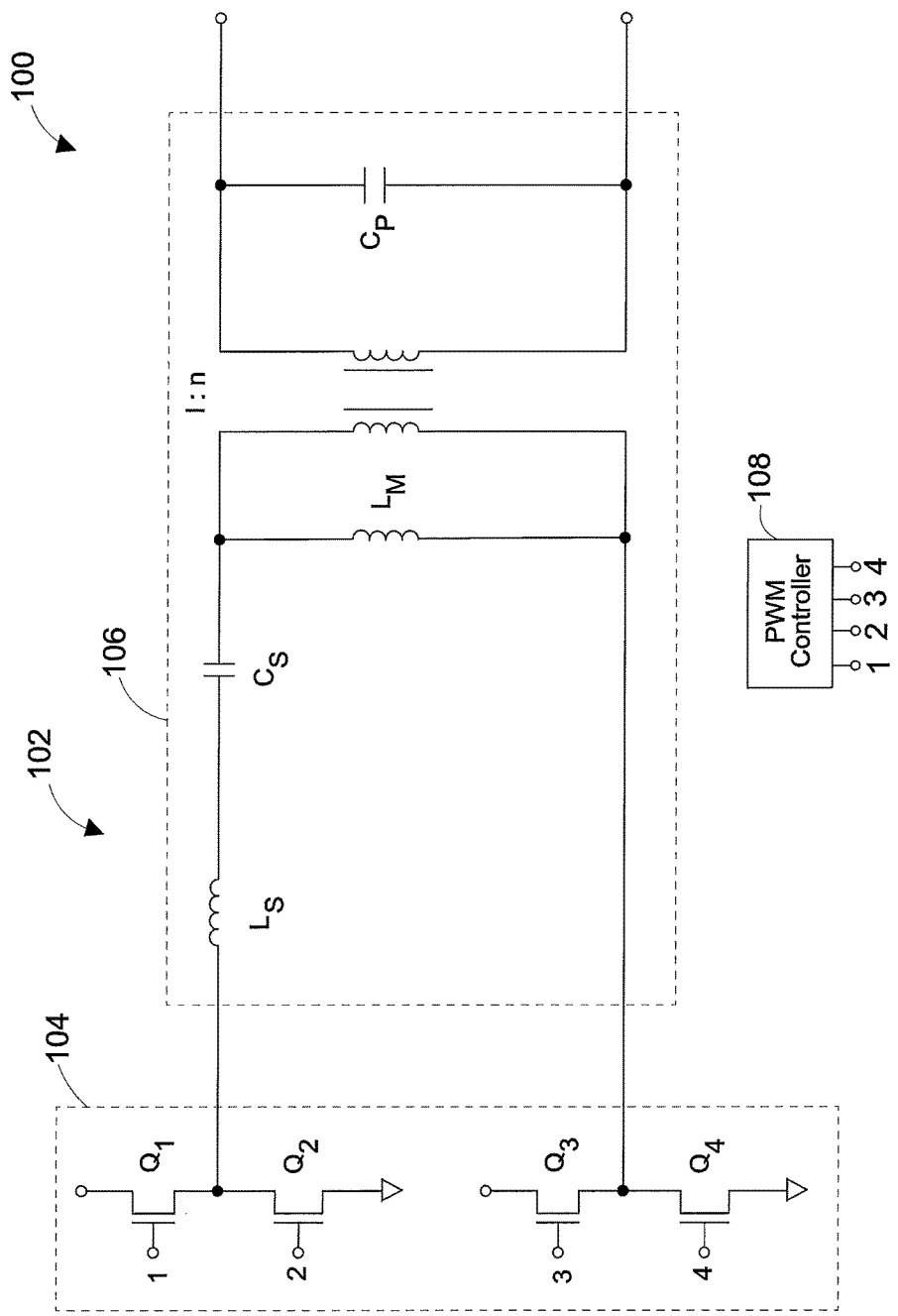
FIG. 1 is a schematic illustration of a prior art electrosurgical generator.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to an electrosurgical generator that employs a phase-shifted full bridge resonant inverter having an LCLC tank topology and an H-bridge. In embodiments of the present disclosure, the number of components in the LCLC tank may be reduced by incorporating the components into the patient isolation transformer of the LCLC tank.

Figure 2:
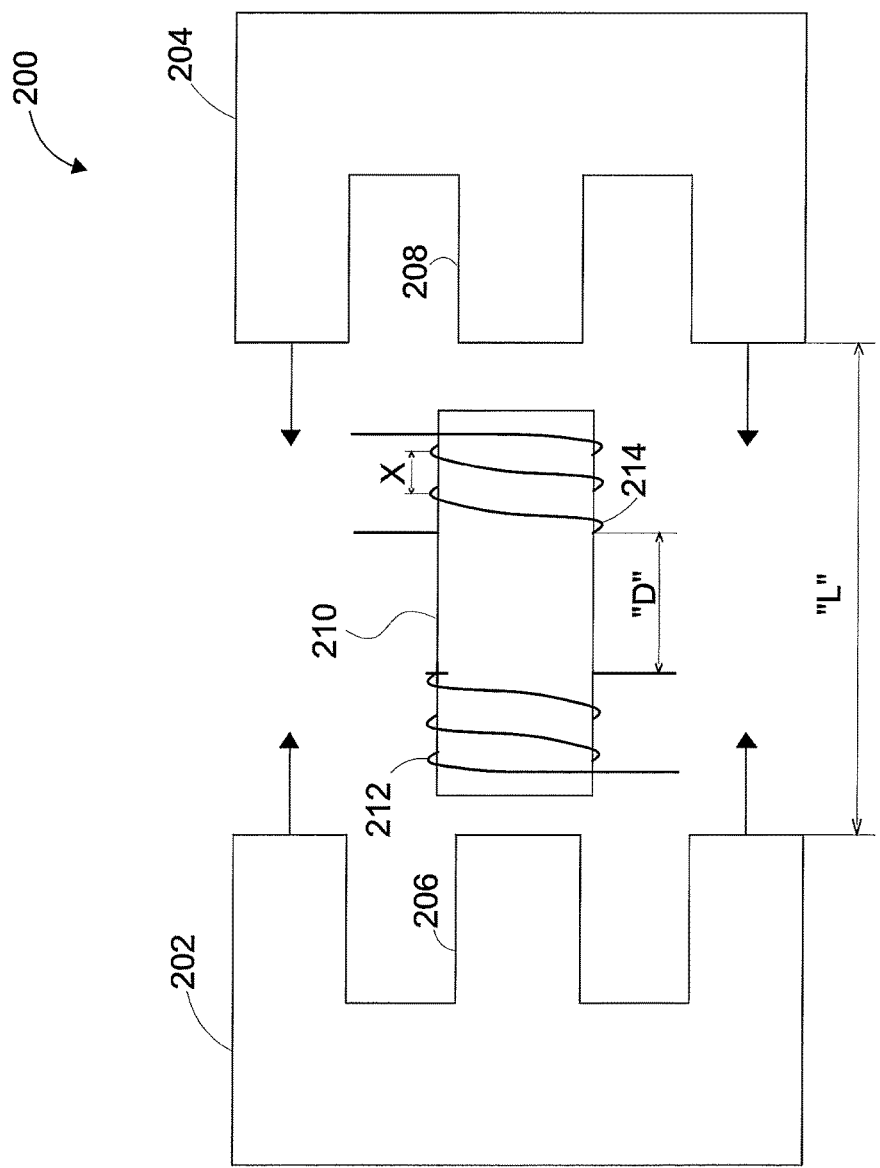
FIG. 2 is an illustration of a transformer for use in the embodiments of the present disclosure.

Turning to FIG. 2, a patient isolation transformer for use in the embodiments described herein is shown generally as 200. Transformer 200 includes a first core half 202 and a second core half 204 that are spaced apart by a gap "L. First core half 202 and second core half 204 may be an industry standard core PQ2625 FERROXCUBE® ferrite core available from FERROXCUBE (formerly a Philips Components company part of the Yageo Corporation). First core half 202 and second core half 204 have respective central members 206 and 208 that are configured to receive a bobbin 210. Bobbin 210 includes a primary winding 212 and a secondary winding 214. The primary winding 212 and the secondary winding 214 are separated by a gap "D". The primary winding 212 and the secondary winding 214 are fabricated from a wire wrapped around the bobbin 210. In the secondary winding 214, the turns of the wire are separated by a gap "X". As will be described below, the gaps "L", "D", and "X" are used to incorporate inductors and capacitors into the design of the transformer to reduce the number of components in the resonant inverter. For example, gap "L" may be used to incorporate a magnetizing inductance, gap "D" may be used to incorporate a leakage inductance, and gap "X" may be used to incorporate a parallel capacitance.

Figure 3:
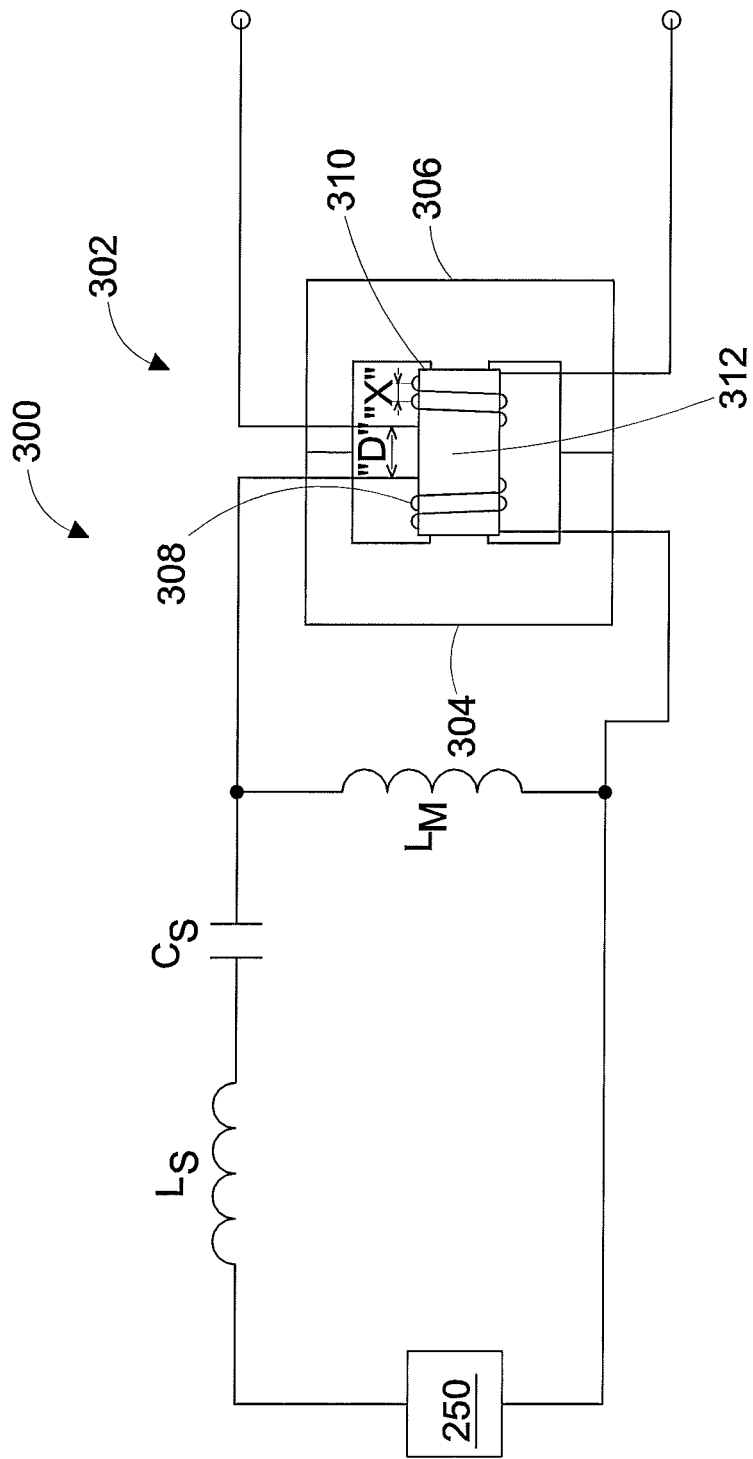
FIG. 3 is a schematic illustration of a resonant inverter for an electrosurgical generator in accordance with an embodiment of the present disclosure.
Figure 4:
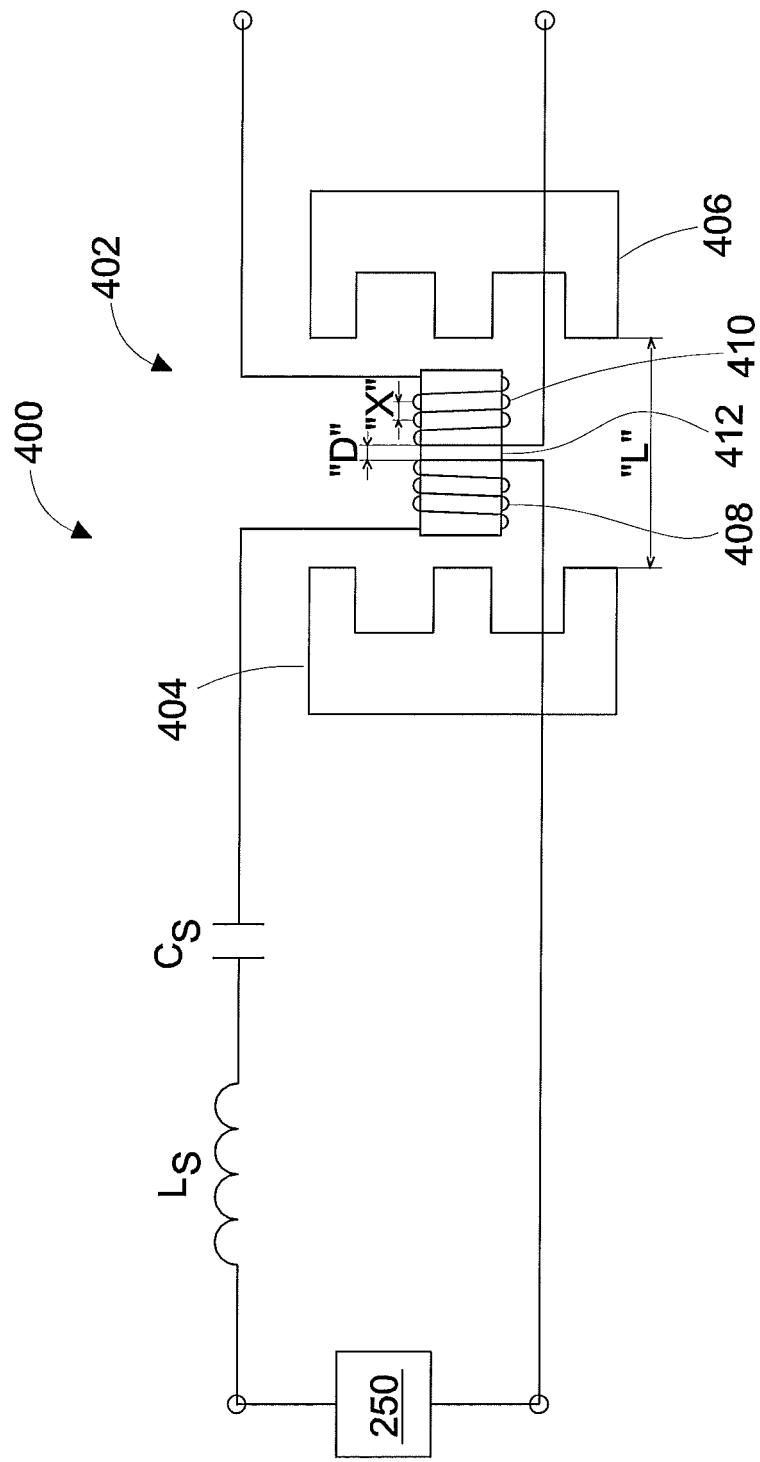
FIG. 4 is a schematic illustration of a resonant inverter for an electrosurgical generator in accordance with another embodiment of the present disclosure.
Figure 5:
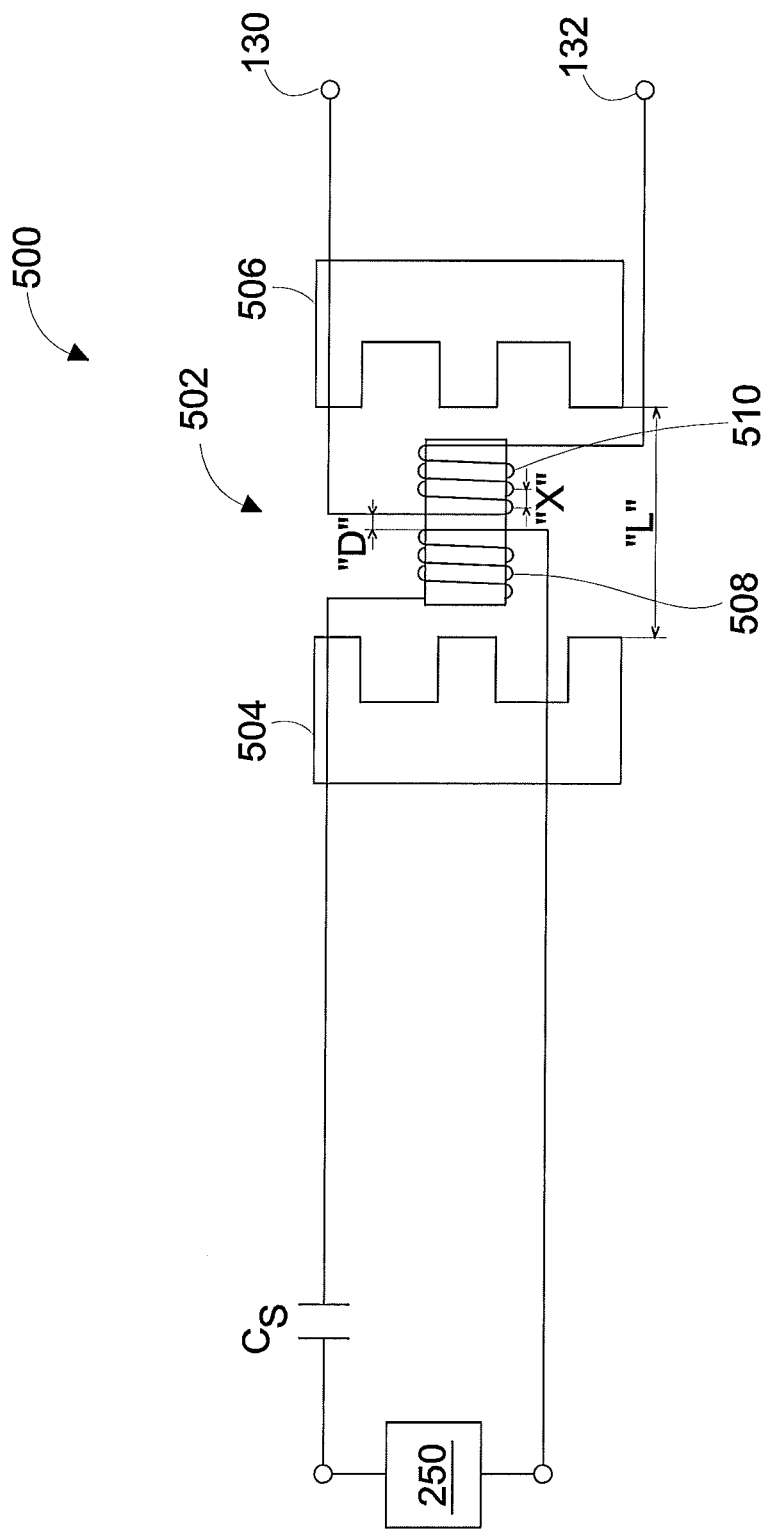
FIG. 5 is a schematic illustration of a resonant inverter for an electrosurgical generator in accordance with yet another embodiment of the present disclosure.

FIGS. 3-5 depict various resonant inverters according to embodiments of the present disclosure. As shown in FIGS. 3-5, the resonant inverters include a RF source 250 to drive a tank. RF source 250 may be similar to H-bridge 104 as shown in FIG. 1.

Turning to FIG. 3, a resonant inverter in accordance with an embodiment of the present disclosure is shown generally as 300. The resonant inverter 300 includes a series inductor $L_S$, a series Capacitor $C_S$, and a parallel inductor $L_M$. The resonant inverter also includes a transformer 302. The transformer 302 includes a first core half 304 and a second core half 306 that abuts the first core half 304. Thus, there is no gap "L" and, as such, the transformer 302 does not incorporate a magnetizing inductance. The transformer 302 also includes a primary winding 308 and a secondary winding 310 wrapped around bobbin 312. The gap "D" between the primary winding 308 and the secondary winding 310 is negligible. Accordingly, the transformer 302 does not incorporate a leakage inductance because the gap "D" is negligible. In the primary winding 308, the gap between turns is arbitrarily large. As such, the primary winding 308 does not incorporate a parallel capacitance on the primary side of the transformer 302. On the other hand, the secondary winding 310 includes a gap "X" between turns of the secondary winding 310 thus incorporating the parallel capacitor $C_P$ of FIG. 1 on the secondary side of the transformer 302 and reducing the number of discrete components needed in the resonant inverter 300. The parallel capacitance is determined based on the gap "X", the dielectric material used in the insulation of the wire that forms the secondary winding 310, and the surface area between turns of the secondary winding 310. The parallel capacitance $C_P$ can be determined by the following equation:

$$C = \varepsilon_r \varepsilon_0 \frac{A}{X}; \quad \text{(Equation 1)}$$

where C is the capacitance; A is the area of overlap of the two conductors; $\varepsilon_r$ is the relative static permittivity (sometimes called the dielectric constant) of the material between the conductors (for a vacuum, $\varepsilon_r$=1); $\varepsilon_0$ is the electric constant ($\varepsilon_0 \approx 8.854 \times 10^{-12}$ F m−1); and X is the separation between the conductors.

Turning to FIG. 4, a resonant inverter in accordance with another embodiment of the present disclosure is shown generally as 400. The resonant inverter 400 includes a series inductor $L_S$ and a series Capacitor $C_S$. The resonant inverter also includes a transformer 402. The transformer 302 includes a first core half 404 and a second core half 406 that are separated by a gap "L". Gap "L" determines a magnetizing inductance thus incorporating the parallel inductor $L_M$ of FIG. 1 and reducing the number of discrete components needed in the resonant inverter 400. The magnetizing inductance $L_M$ can be determined by the following equation:

$$L_M = u \times n^2 \times \frac{A_C}{L}; \quad \text{(Equation 2)}$$

where $u=u_r \times u_0$ (relative permeability times permeability of free space); n=turns on primary; $A_c$= cross-sectional area of gap; and L= length of gap. The transformer 402 also includes a primary winding 408 and a secondary winding 410 wrapped around bobbin 412. The gap "D" between the primary winding 408 and the secondary winding 410 is negligible. Accordingly, the transformer 402 does not incorporate a leakage inductance because the gap "D" is negligible. Similar to transformer 302, the gap between turns is in the primary winding 408 is arbitrarily large and the secondary winding 410 includes a gap "X" between turns of the secondary winding 410 thus incorporating a parallel capacitance on the secondary side of the transformer 402.

Turning to FIG. 5, a resonant inverter in accordance with yet another embodiment of the present disclosure is shown generally as 500. The resonant inverter 500 includes a series capacitor $C_S$ and a transformer 502. Similar to transformer 402, the transformer 502 includes a gap "L between first core half 504 and second core half 506 to include a magnetizing inductance and a gap "X" between turns of a secondary winding 510 to include a parallel capacitance on the secondary side of the transformer 502. The transformer 502 also includes a gap "D" between a primary winding 508 and the secondary winding 510. The distance "D" determines a leakage inductance thus incorporating the series inductor $L_S$ of FIG. 1 and reducing the number of discrete components needed in the resonant inverter 502. The relationship between the distance "D" and the leakage inductance $L_S$ is determined empirically. Thus, when compared to the resonant inverter 102 of FIG. 1 which needs five discrete components in the tank 106, the resonant inverter 502 only needs two components in the tank thereby reducing the cost of the resonant inverter as well as the complexity.

The resonant inverters described in FIGS. 3-5 can be included in an electrosurgical generator in accordance with embodiments of the present disclosure. The generator includes suitable input controls (e.g., buttons, activators, switches, touch screen, etc.) for controlling the generator. In addition, the generator may include one or more display screens (not shown) for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). An instrument (not shown) that may be connected to the generator may also include a plurality of input controls that may be redundant with certain input controls of the generator. Placing the input controls at the instrument allows for easier and faster modification of RF energy parameters during the surgical procedure without requiring interaction with the generator.

The generator may include a plurality of connectors to accommodate various types of electrosurgical instruments. Further, the generator may operate in monopolar or bipolar modes by including a switching mechanism (e.g., relays) to switch the supply of RF energy between the connectors.

The embodiments described above are merely examples of the different resonant inverters that may be used in an electrosurgical generator. Based on the principles outlined above, the transformer may be designed to replace any of the discrete components in multiple combinations. For instance, the transformer may be used to replace, the series inductor, the parallel inductor, the parallel capacitor, the series inductor and the parallel inductor, the series inductor and the parallel capacitor, the parallel inductor and the parallel capacitor, or all three components.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical generator comprising:
   a tank configured to output energy, wherein the tank functions as an LCLC tank;
   an H-bridge configured to drive the tank;
   a transformer including:
      a first core half;
      a second core half;
      a primary winding; and
      a secondary winding having a number of turns, wherein each turn is separated by a constant gap; and
   a bobbin coupled to the first core half and the second core half,
   wherein the secondary winding is disposed on the bobbin,
   wherein the constant gap provides a parallel capacitance of the LCLC tank, the parallel capacitance being in parallel with a secondary side of the transformer, and
   wherein the secondary winding is the only component of the tank that provides the parallel capacitance such that the parallel capacitance is not provided by any discrete component.

2. The electrosurgical generator of claim 1, wherein the primary winding is disposed on the bobbin.

3. An electrosurgical generator comprising:
   a tank configured to output energy, wherein the tank functions as an LCLC tank;
   an H-bridge configured to drive the tank;
   a transformer including:
      a first core half;
      a second core half separated from the first core half by a first gap;
      a primary winding; and
      a secondary winding having a number of turns, wherein each turn is separated by a constant gap; and
   a bobbin coupled to the first core half and the second core half,
   wherein the secondary winding is disposed on the bobbin,
   wherein the first gap provides a magnetizing inductance of the LCLC tank and the constant gap provides a parallel capacitance of the LCLC tank, the magnetizing inductance being in parallel with a primary side of the transformer and the parallel capacitance being in parallel with a secondary side of the transformer,
   wherein the transformer is the only component of the tank that provides the magnetizing inductance such that the magnetizing inductance is not provided by any discrete component, and
   wherein the secondary winding is the only component of the tank that provides the parallel capacitance such that the parallel capacitance is not provided by any discrete component.

4. The electrosurgical generator of claim 3, wherein the primary winding is disposed on the bobbin.

5. An electrosurgical generator comprising:
   a tank configured to output energy, wherein the tank functions as an LCLC tank;
   an H-bridge configured to drive the tank;
   a transformer including:
      a first core half;
      a second core half separated from the first core half by a first gap;
      a primary winding; and
      a secondary winding separated from the primary winding by a second gap, the secondary winding having a number of turns, wherein each turn is separated by a constant gap; and
   a bobbin coupled to the first core half and the second core half,
   wherein the secondary winding is disposed on the bobbin,
   wherein the first gap provides a magnetizing inductance of the LCLC tank, the second gap provides a series inductance of the LCLC tank, and the constant gap provides a parallel capacitance of the LCLC tank, wherein the transformer is the only component of the tank that provides the magnetizing inductance such that the magnetizing inductance is not provided by any discrete component, wherein the transformer is the only component of the tank that provides the series inductance such that the series inductance is not provided by any discrete component, and wherein the secondary winding is the only component of the tank that provides the parallel capacitance such that the parallel capacitance is not provided by any discrete component.

6. The electrosurgical generator of claim 5, wherein the primary winding is disposed on the bobbin.

7. The electrosurgical generator of claim 5, wherein:

the magnetizing inductance is in parallel with a primary side of the transformer;

the parallel capacitance being in parallel with a secondary side of the transformer; and the series inductance is in series with the primary side of the transformer.

\* \* \* \* \*